United States Patent [19]

Verkade

[11] Plant 4,794

[45] Nov. 24, 1981

[54] *PIERIS JAPONICA* NAMED CRYSTAL

[76] Inventor: Gerald H. Verkade, Rear 13, Lower Blvd., New London, Conn. 06320

[21] Appl. No.: 163,784

[22] Filed: Jun. 27, 1980

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Rummler and Snow

[57] ABSTRACT

A new variety of Pieris bush characterized by the dark green leaves which are extremely thick, deeply serrated, have a waxy appearance when mature and remain glossy all year round.

3 Drawing Figures

BACKGROUND OF THE INVENTION

My new Pieris bush originated as a seedling growing in a landscape of *Pieris japonica* in a cultivated area in New London, Conn. Cuttings were rooted and plants have been asexually reproduced by me at New London, Conn., since 1970. Present propagation is done at Verkade's Nursery, Inc., Waterford, Conn. Propagation has been continued since 1970 because the leaves were thick and possessed a dark green color having a shiny, waxy upper surface not found in *P. japonica,* and after several generations, the distinguishing features remain fixed and hold true from generation to generation.

BRIEF DESCRIPTION OF THE DRAWINGS

My new variety of Pieris plant is illustrated by the accompanying photographic drawings.

On the first sheet with two photographs thereon, the upper photograph shows substantially the entire variety as it appears in sunlight.

The lower figure is a close-up view of the leaves of the present invention.

The second sheet of photographs shows a close-up of the flowers.

DESCRIPTION OF THE NEW PLANT

The following is a detailed description of the new variety of Pieris plant with color designations according to The RHS Colour Chart published by The Royal Horticultural Society of London, England.

THE PLANT

Origin: Seedling.
Parentage: Seed and pollen parent were *Pieris japonica.*
Botanical name: *Pieris japonica.*
Commercial name: Japanese Andromeda.
Form: Bush.
Shape: Globose.
Height: 1.4 m. (4 feet).
Growth habit: 15 cm. per year (6 inches).
Foliage:

*Leaves.*—Quantity: Generous. Size: 5 to 6.5 cm. long by 1.8 to 2.4 cm. wide. Form: Ovate to oblong; lanceolate. Margin type: Distal two-thirds more toothed than typical for species. Color: Upper side — Dark Green 147A. Lower side — 146A or B. Upper mid-vein — 144A. Pedicel of upper leaves — 59A. Angle of leaf blade base: 50° to 55°. Pubescence: Distribution — Scattered glandular hairs most prevalent on both sides.

FLOWER BUDS

Blooming period: Early spring.
Quantity: Moderate annual bloomer but not floriferous.
Size: Medium.
Borne: In terminal panicles.
Color: White.

*Sepals.*—Bud closed — 59B. Open flower — 145B.

REPRODUCTIVE ORGANS

Pollen: Present but probably nonfunctional.
Seeds: None.

This new variety most resembles typical *P. japonica* in habit and in superficial traits. However, there are distinctive differences from the species in that the leaves are thick, undulated and dark green with a shiny, waxy upper surface. The leaf blade is about 28% thicker and the leaf stomates (only under magnification) are 50% larger. The thick, leathery leaves and large stomates indicate the plant may be polyploid (triploid, or possible tetraploid). That is, the chromosome number is likely to be in excess of the normal 2n=24 for the species. The plant is a moderate but annual bloomer. It is sterile and sets no seed.

I claim:

1. A new and distinctive variety of Pieris plant substantially as herein shown and described, characterized by an abundant seedless flowering, its leaves being extremely thick, having an undulated, dark green color and having a shiny wax surface and remains glossy all year round.

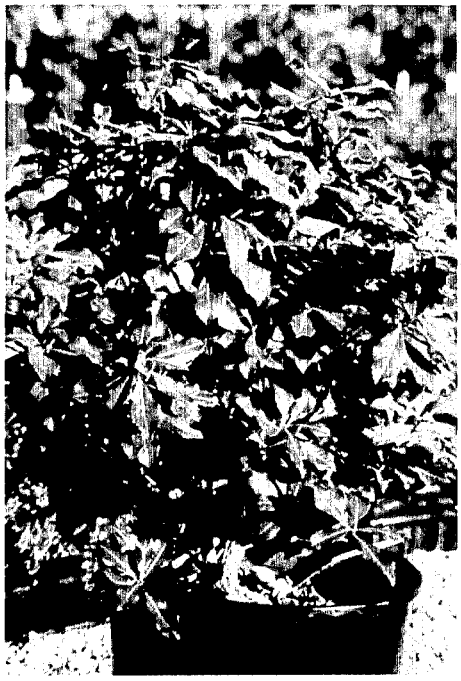
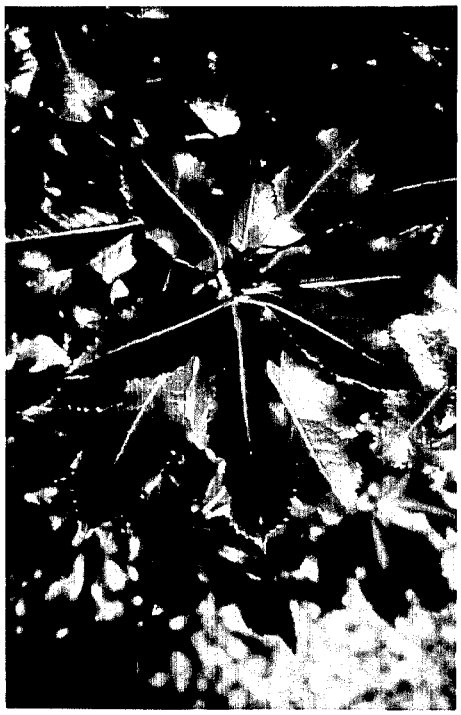

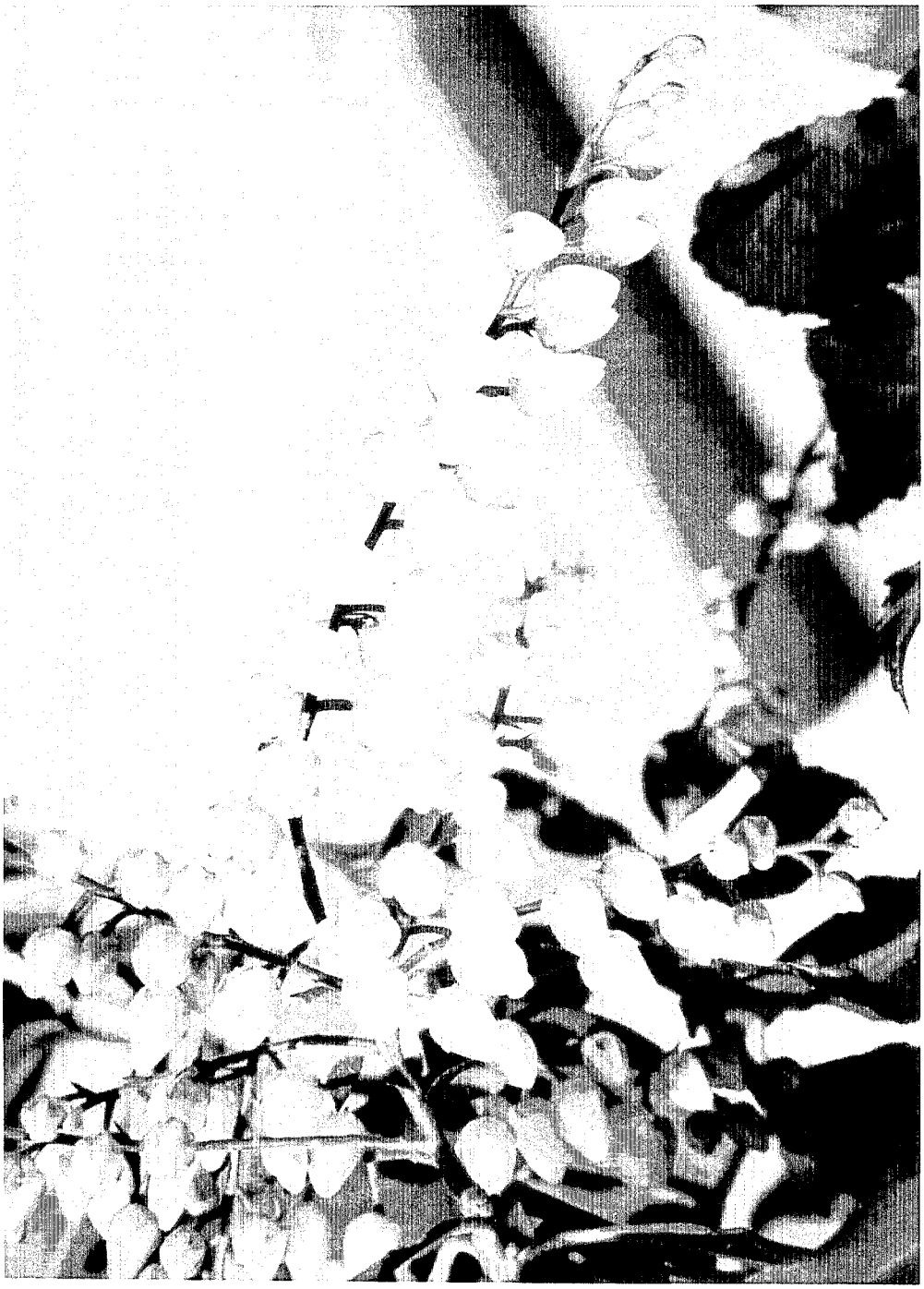

* * * * *